United States Patent [19]
Van Es et al.

[11] Patent Number: 5,111,496
[45] Date of Patent: May 5, 1992

[54] X-RAY EXAMINATION TABLE WITH PIVOTALLY CONNECTED FILM HOLDER

[75] Inventors: Ludovicus P. C. Van Es; Robert Van Der Ploeg, both of Eindhoven, Netherlands

[73] Assignee: U.S. Philips Corporation, New York, N.Y.

[21] Appl. No.: 518,881

[22] Filed: May 4, 1990

[30] Foreign Application Priority Data

May 10, 1989 [NL] Netherlands .................. 8901169

[51] Int. Cl.$^5$ ............................................. G03B 42/02
[52] U.S. Cl. ..................................... 378/177; 378/181; 378/209
[58] Field of Search ............... 378/167, 172, 173, 177, 378/181, 195, 209, 178, 190, 196

[56] References Cited

U.S. PATENT DOCUMENTS

| | | | |
|---|---|---|---|
| 2,504,687 | 4/1950 | Hollstein | 378/177 |
| 4,232,227 | 11/1980 | Finkenzeller et al. | 378/177 |
| 4,365,344 | 12/1982 | Dornheim | 378/209 |
| 4,761,805 | 8/1988 | Sebring | 378/181 |
| 4,829,986 | 5/1989 | Eichler et al. | 378/181 |
| 4,879,736 | 11/1989 | Bergman et al. | 378/181 |

FOREIGN PATENT DOCUMENTS

| | | |
|---|---|---|
| 0297355 | 6/1988 | European Pat. Off. . |
| 1939557 | 6/1970 | Fed. Rep. of Germany . |
| 2346102 | 1/1975 | Fed. Rep. of Germany . |

*Primary Examiner*—Janice A. Howell
*Assistant Examiner*—Kim-Kwok Chu
*Attorney, Agent, or Firm*—William Squire

[57] ABSTRACT

A film holder is pivotably connected to a table frame of a patient table. By positioning the film holder so that an image plane thereof extends parallel to the table top, X-ray images can be recorded on film. In the folded-up condition, the image plane of the film holder extends parallel to the table frame so that the film holder does not form an obstruction for the formation of X-ray images by means of an X-ray image intensifier tube. The position of the film holder enables a fast change-over from exposures using an X-ray image intensifier tube to recording on film.

7 Claims, 1 Drawing Sheet

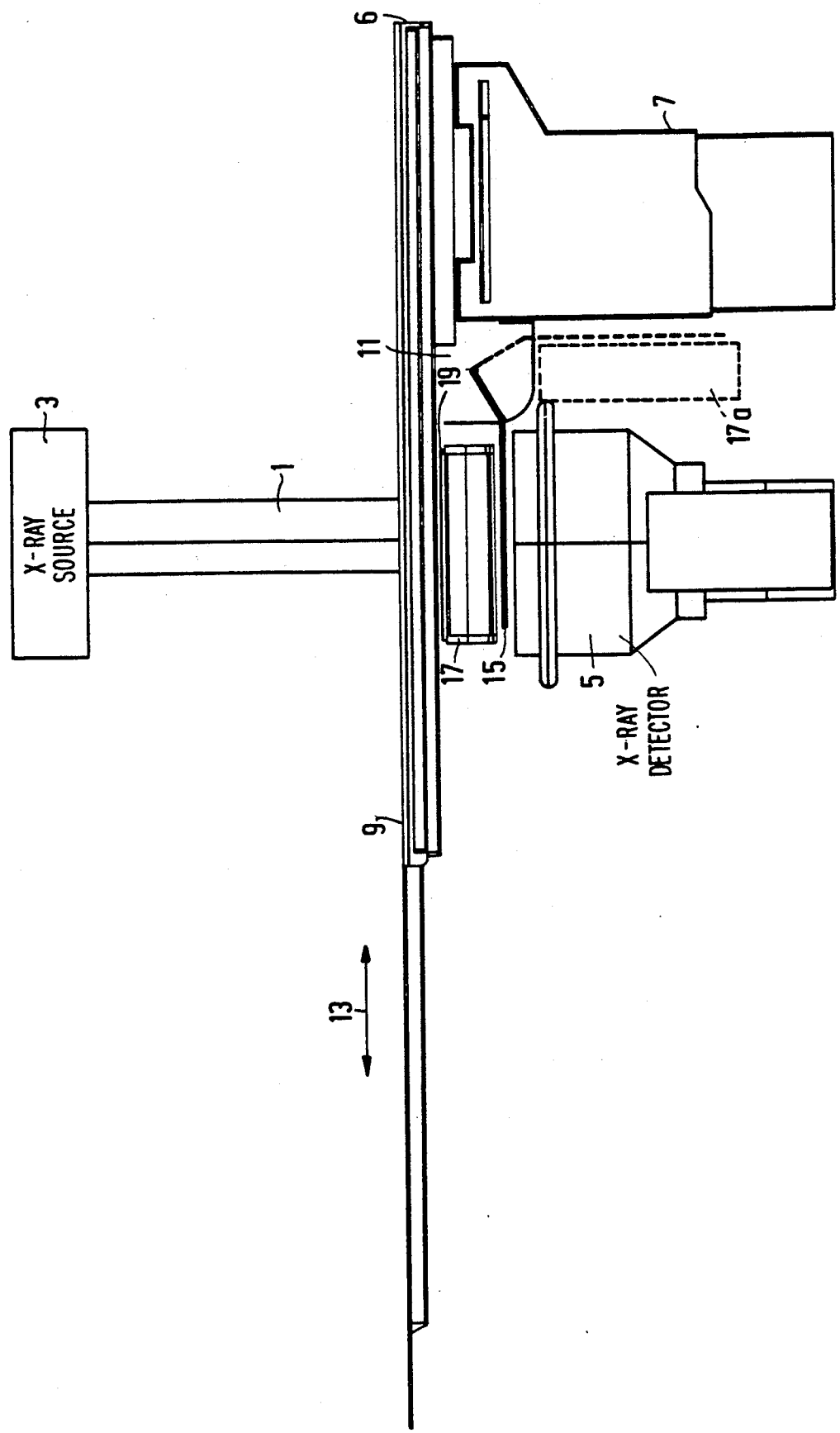

X-RAY EXAMINATION TABLE WITH PIVOTALLY CONNECTED FILM HOLDER

The invention relates to an X-ray examination apparatus, comprising an X-ray source and an X-ray detector which are mounted on a carrier so that they face one another, and also comprising a patient table with a table frame and a table top supported by the table frame.

An X-ray examination apparatus of this kind is known from the European Patent Application EP 297 355.

The cited Patent Application describes an X-ray examination apparatus with an X-ray source and an X-ray detector in the form of an X-ray image intensifier tube which are connected to a C-arm. For the imaging of, for example blood vessels in limbs of a patient arranged on the patient table, the X-ray examination apparatus is displaceable in a longitudinal direction of the patient table. The X-ray image intensifier tube is then situated underneath the patient table and the table top is stationary. For the recording of X-ray images on an X-ray-sensitive film, for example for diagnostic or filing purposes, a mobile frame whereto a film cassette is connected can be coupled to the X-ray image intensifier tube. The film cassette comprises a film changer for transporting the film in cooperation with the X-ray source, so that an X-ray image can be recorded in a number of positions in a longitudinal direction of the patient table. An X-ray examination apparatus of this kind has the drawback that the film cassette must be coupled to the X-ray image intensifier tube by way of the frame prior to the recording of an X-ray image on film. The use of such a film cassette, connected to a mobile frame, is comparatively cumbersome because the frame must be correctly positioned with respect to the X-ray image intensifier tube and leads for power supply and synchronization of film transport and exposure time must be secured. Moreover, when not in use, the loose carrier with the film cassette forms an obstacle in the examination room.

It is inter alia an object of the invention to provide an X-ray examination apparatus in which a film holder can be exchanged with an X-ray detector, notably an X-ray image intensifier tube, in a simple and efficient manner.

To achieve this, an X-ray examination apparatus in accordance with the invention is characterized in that a film holder is pivotably connected to the table frame, it being possible to position an image plane in the film holder to extend parallel to the table top as well as transversely of the table top by pivoting, the table top being displaceable in a longitudinal direction with respect to the table frame.

Because the film holder is pivotably connected to the table frame, the film holder can be readily pivoted from a position in which it bears against the table frame and in which the film holder does not form an obstacle for the X-ray detector, to a position which is suitable for exposure. The film holder preferably comprises a film changer for film transport when a plurality of exposures are made. Because connections for power supply and synchronization of the film changer are accommodated in the frame so as to be permanently connected, a fast change-over from X-ray imaging using an X-ray image intensifier tube to X-ray imaging using a film is possible.

An embodiment of an X-ray examination apparatus will be described in detail hereinafter with reference to the accompanying drawing.

The drawing shows a side elevation of an X-ray examination apparatus in accordance with the invention.

An X-ray source 3 and an X-ray detector 5, for example an X-ray image intensifier tube, are connected to a carrier 1, for example a C-arm. The carrier 1 is connected to a ceiling or a floor of an examination space so as to be movable with respect to a patient table 6. The patient table 6 comprises a table frame 7 and a table top 9 which is movably connected to the table frame 7. A film holder 17 is pivotably connected, by way of a bracket 15, to a mounting portion 11 which is formed, for example by a housing of a drive motor which is not shown in the Figure and which cooperates with the table top 9. An object arranged on the table top 9, for example a patient, can be irradiated by the X-ray source 3 from a plurality of directions by correctly positioning the carrier 1. The X-rays attenuated by the object are converted into an optical image by the X-ray detector 5. For the imaging of, for example blood vessels of a patient, the X-ray source 3 and the X-ray detector 5 are displaced in a longitudinal direction 13, parallel to the table top 9, so as to obtain an X-ray image in different positions within a patient. A feasible position occupied by the X-ray detector during such a displacement is situated just underneath the table top 9. So as not to impede the freedom of movement of the X-ray detector with respect to the patient, the film holder 17 is folded back against the table frame 7 into a position 17a denoted by a broken line. In this position of the film holder 17 an image plane 19 in the film holder extends transversely of the table top 9. In order to make X-ray images using an X-ray-sensitive film contained in the film holder 17, the film holder 17 is positioned, using the bracket 15 which also serves as a grip, so that the image plane 19 extends parallel to the table top 9. Parts of the object to be imaged can be positioned over the film holder by displacement of the table top 9 in the direction 13, enabling the recording on the X-ray-sensitive film. After film transport, during which a new film is introduced into the film holder 17 by a film changer (not shown in the Figure), a next image of another part of the patient can be formed. In order to check whether a part of the object to be imaged is situated in the image plane 19 of the film holder 17, a test exposure can be made before the film changer introduces the film into the film holder 17, the X-ray detector 5 then being situated underneath the film holder 17. Cables for powering the film changer connected to the film holder and cables for synchronization signals for synchronizing the operation of the X-ray source 3 and the film transport are accommodated in the table frame 7.

We claim:

1. An X-ray examination apparatus comprising an X-ray source, an X-ray detector, said source and detector being mounted on a carrier so that they face one another, and a patient table with a table frame and a table top supported by the table frame, the combination therewith comprising a film holder having an image plane and pivotally connected to the table frame for pivoting to first and second positions relative to the frame and means securing the film holder such that the image plane of the film holder extends parallel to the table top in the first position and transversely of the table top in the second position, said frame including means for permitting the table top to displace in a given direction with respect to the table frame.

2. An X-ray examination apparatus as claimed in claim 1, characterized in that the film holder comprises a film changer.

3. The apparatus of claim 1 wherein said means for permitting includes means for permitting the table top to displace parallel to the first position.

4. An X-ray examination apparatus comprising:
an X-ray source;
an X-ray detector for detecting X-rays radiated by the source;
a table frame;
a patient table movably secured to the frame;
an X-ray film holder defining a film image plane; and
means for pivotally securing the film holder to the table frame for permitting the holder to pivot to first and second positions so that in the first position the image plane is parallel to the table and in the second position the image plane extends transverse said table.

5. The apparatus of claim 4 wherein said detector is an image intensifier tube.

6. The apparatus of claim 4 including means for permitting the table to displace in a direction parallel to the image plane of said holder in the first position.

7. The apparatus of claim 4 wherein said holder comprises a film changer.

* * * * *